United States Patent
Corrado

(10) Patent No.: US 6,622,862 B1
(45) Date of Patent: Sep. 23, 2003

(54) CONTAINER SYSTEM FOR FLASH AND CONVENTIONAL STERILIZATION

(76) Inventor: Pasquale A. Corrado, 497 - 79th St. S., St. Petersburg, FL (US) 33707

( * ) Notice: Subject to any disclaimer, the term of this patent is extended or adjusted under 35 U.S.C. 154(b) by 0 days.

(21) Appl. No.: 10/083,943

(22) Filed: Feb. 27, 2002

(51) Int. Cl.⁷ .............................................. B65D 83/10
(52) U.S. Cl. ...................... 206/363; 206/438; 206/439; 220/367.1; 220/324; 220/720; 220/201; 422/300
(58) Field of Search ................................ 206/363, 368, 206/369, 370, 364, 366, 438, 439, 524.8; 220/720, 721, 203.16, 203.11, 203.12, 203.15, 367.1, 369–372, 378, 324, DIG. 27, 201; 422/300, 310, 292, 297

(56) References Cited

U.S. PATENT DOCUMENTS

| | | | | |
|---|---|---|---|---|
| 2,643,024 A | * | 6/1953 | Cronheim ................. | 220/367.1 |
| 4,783,321 A | * | 11/1988 | Spence ....................... | 422/300 |
| 5,277,876 A | * | 1/1994 | Wagner ...................... | 422/110 |
| 5,324,489 A | * | 6/1994 | Nichols et al. ............. | 422/292 |
| 5,968,459 A | * | 10/1999 | Nalepa et al. .............. | 422/300 |
| 6,186,178 B1 | * | 2/2001 | Darroux ...................... | 138/30 |
| 6,350,418 B1 | * | 2/2002 | Venderpool et al. ........ | 422/297 |

FOREIGN PATENT DOCUMENTS

EP       152544 A2 * 8/1985   ............. A61L/2/26

* cited by examiner

*Primary Examiner*—J. Mohandesi
(74) *Attorney, Agent, or Firm*—Edward P. Dutkiewicz

(57) ABSTRACT

A sterilization container system comprises a lid. The container system has a wall positionable on a tray. The lid has a large aperture and small attachment apertures. A support is formed with an interior central circular disk. An exterior circular ring is provided. Ribs connect the ring and the disk. The disk has a central aperture. Small attachment apertures are provided for coupling the upper surface of the ring to the lower surface of the wall. A thin plate has a central aperture and a periphery. Also provided is a spring positioned between the disk and the plate. The spring and plate are adapted to expand when heated. A space is created between the plate and the disk whereby medical instruments within the container system will be sterilized. The spring and plate are adapted to contract when cooled. Any space between the plate and the disk will be eliminated.

8 Claims, 5 Drawing Sheets

CONTAINER SYSTEM FOR FLASH AND CONVENTIONAL STERILIZATION

BACKGROUND OF THE INVENTION

Field of the Invention

The present invention relates to a sterilization container system and more particularly pertains to safely and conveniently sterilizing medical instruments in an autoclave.

Description of the Prior Art

The use of sterilization systems of known designs and configurations is known in the prior art. More specifically, sterilization systems of known designs and configurations previously devised and utilized for the purpose of sterilizing medical instruments through conventional methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,748,003 to Riley discloses a container for flash sterilization. U.S. Pat. No. 4,915,913 to Williams et al. discloses a medical sterilizer device with improve latch mechanism. U.S. Pat. No. 5,097,865 to Riley discloses a valved flash sterilization container. U.S. Pat. No. 5,540,901 to Riley discloses a sterilization tray system for surgical instruments. U.S. Pat. No. 5,896,882 to McGrath, Jr. discloses a pressure control valve. Lastly, U.S. Pat. No. 6,048,503 to Riley et al. discloses a sterilization container.

While these devices fulfill their respective, particular objectives and requirements, the aforementioned patents do not describe a sterilization container system that allows safely and conveniently sterilizing medical instruments.

In this respect, the sterilization container system according to the present invention substantially departs from the conventional concepts and designs of the prior art, and in doing so provides an apparatus primarily developed for the purpose of safely and conveniently sterilizing medical instruments in an autoclave.

Therefore, it can be appreciated that there exists a continuing need for a new and improved sterilization container system which can be used for safely and conveniently sterilizing medical instruments in an autoclave. In this regard, the present invention substantially fulfills this need.

SUMMARY OF THE INVENTION

In view of the foregoing disadvantages inherent in sterilization systems of known designs and configurations now present in the prior art, the present invention provides an improved sterilization container system. As such, the general purpose of the present invention, which will be described subsequently in greater detail, is to provide a new and improved sterilization container system and method which has all the advantages of the prior art and none of the disadvantages.

To attain this, the present invention essentially comprises a bottom tray. The bottom tray is formed in a generally rectilinear configuration. The bottom tray has a rectangular horizontal bottom wall and rectangular vertical up-standing walls. The walls terminate in an upper periphery with an open top. In this manner a reception area is formed within the tray for receiving medical instruments to be sterilized. The up-standing walls of the bottom tray include long side walls and short end walls. The end walls include releasable clamps. A lid is provided. The lid is formed in a generally rectilinear configuration. The lid has a rectangular horizontal upper wall and rectangular vertical depending walls. The walls terminate in a lower periphery with an open bottom positionable on the upper periphery of the tray. The depending walls of the lid include long side walls and short end walls. The end walls include reception areas for the releasable clamps to allow locking of the lid to the tray during operation and use. The lid has a large circular aperture through the upper wall. Small attachment apertures are provided through the upper wall adjacent to the large circular aperture. Provided next is a domed support. The domed support is formed with an interior central circular disk and an exterior circular ring. Four ribs are provided in a crossing configuration connecting the ring and the disk. The disk has a central aperture there through. A plurality of small attachment apertures are provided through the ring. The apertures are aligned with the small attachment apertures of the lid. Bolts are provided through the attachment apertures of the lid and ring. Associated nuts couple the upper surface of the ring to the lower surface of the upper wall of the lid. The domed support is fabricated of thick stainless steel to preclude expansion upon the application of sterilization heat. The ribs are bowed upwardly to extend through the large aperture of the lid and above the upper surface of the lid. Also provided is a thin dome shaped plate. The plate has an upper surface in contact with the lower surface of the support. The plate is fabricated of a specialty metal. The specialty metal is selected from the class of specialty metals including a nickel alloy and INVAR. INVAR is a trademark of STE. AME. De Commentry Fourchambault Et Decazeville Corporation and relates to an alloy which is substantially inexpansible. Other combinations of metals may be used, i.e., stainless steel and copper. Stainless steel and INVAR need not be plated to protect against corrosion; however, other combinations may perform better if protected from corrosion. The plate has a central aperture. The periphery of the plate is positionable adjacent to the lower surface of the ring. The plate is adapted to expand upon the application of sterilization heat. In this manner the periphery will move away from the lower surface of the ring. Provided next is an elastomeric seal. The seal is coupled to the lower surface of the ring. The seal has an annular recess. The annular recess is formed in the lower surface of the ring for receiving the seal. The seal has a downwardly extending point for contacting the periphery of the plate. An annular elastomeric gasket is provided next. The gasket is positioned between the ring and the lid. Small attachment apertures are provided in the gasket. The apertures of the gasket are aligned with the attachment apertures of the lid and the ring. Further provided is a U-shaped spring. The spring is also fabricated from a bi-metal. It will be the same material as the disk. The spring is positioned between the disk and the plate. The spring has an upper aperture. The upper aperture is aligned with the aperture of the disk. A bolt is provided there through. An associated nut is also provided. The spring has a lower aperture. The lower aperture is aligned with the aperture of the plate. A bolt is provided there through. An associated nut is further provided. The spring couples the plate to the support. The spring and plate are adapted to expand when heated to between about 135 and 272 degrees Fahrenheit, preferably about 135 degrees Fahrenheit up to a sterilization temperature of about 275 degrees Fahrenheit. In this manner a space is created between the plate and the disk whereby medical instruments within the container may be sterilized. The spring and plate are adapted to close when cooled to about 135 degrees Fahrenheit. Temperatures below 135 degrees Fahrenheit reverse the direction of the spring and disk and create a tighter seal against the seal. In this manner any space between the plate and the disk may be eliminated. Next provided is a pressure equalizing valve in the lid. The valve is provided to relieve pressure from the container while heating or cooling. Lastly, a protective guard is provided. The guard is fabricated of stainless steel and formed in two layers. Each layer is perforated with holes preferably of 1/8 inch diameter with centers staggered at about 3/16 inch apart. The holes in the layers are not aligned. The guard is provided to preclude inadvertent manual opening of the valve.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved flash and conventional sterilization container system which has all of the advantages of the prior art sterilization systems of known designs and configurations and none of the disadvantages.

It is another object of the present invention to provide a new and improved flash and conventional sterilization container system which may be easily and efficiently manufactured and marketed.

It is further an object of the present invention to provide a new and improved flash and conventional sterilization container system which is of durable and reliable constructions.

An even further object of the present invention is to provide a new and improved flash and conventional sterilization container system which is susceptible of a low cost of manufacture with regard to both materials and labor, and which accordingly is then susceptible of low prices of sale to the consuming public, thereby making such flash and conventional sterilization container system economically available to the medical community.

Even still another object of the present invention is to provide a flash and conventional sterilization container system for safely and conveniently sterilizing medical instruments in an autoclave.

Lastly, it is an object of the present invention to provide a new and improved flash and conventional sterilization container system comprising a lid. The container system has a wall positionable on a tray. The lid has a large aperture and small attachment apertures. A support is formed with an interior central circular disk. An exterior circular ring is provided. Ribs connect the ring and the disk. The disk has a central aperture. Small attachment apertures are provided for coupling the upper surface of the ring to the lower surface of the wall. A thin plate has a central aperture and a periphery. Also provided is a spring positioned between the disk and the plate. The spring and plate are adapted to expand when heated. A space is created between the plate and the disk whereby medical instruments within the container system may be sterilized. The spring and plate are adapted to contract when cooled. Any space between the disk and the seal will be eliminated.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
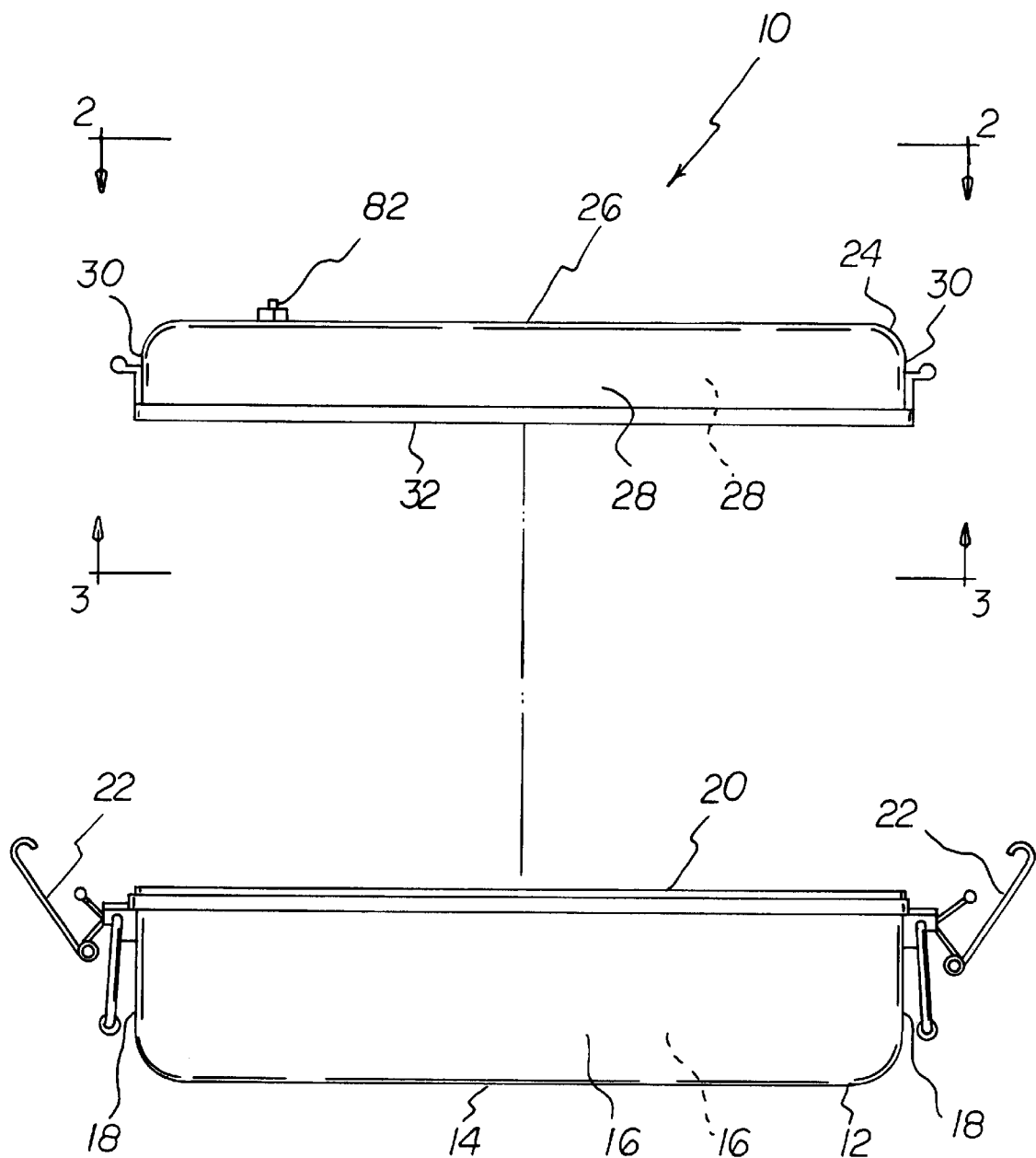
FIG. 1 is an exploded side elevational view of a container system for flash and conventional sterilization, safely and conveniently, in an autoclave, the container system being constructed in accordance with the principles of the present invention.
Figure 2:
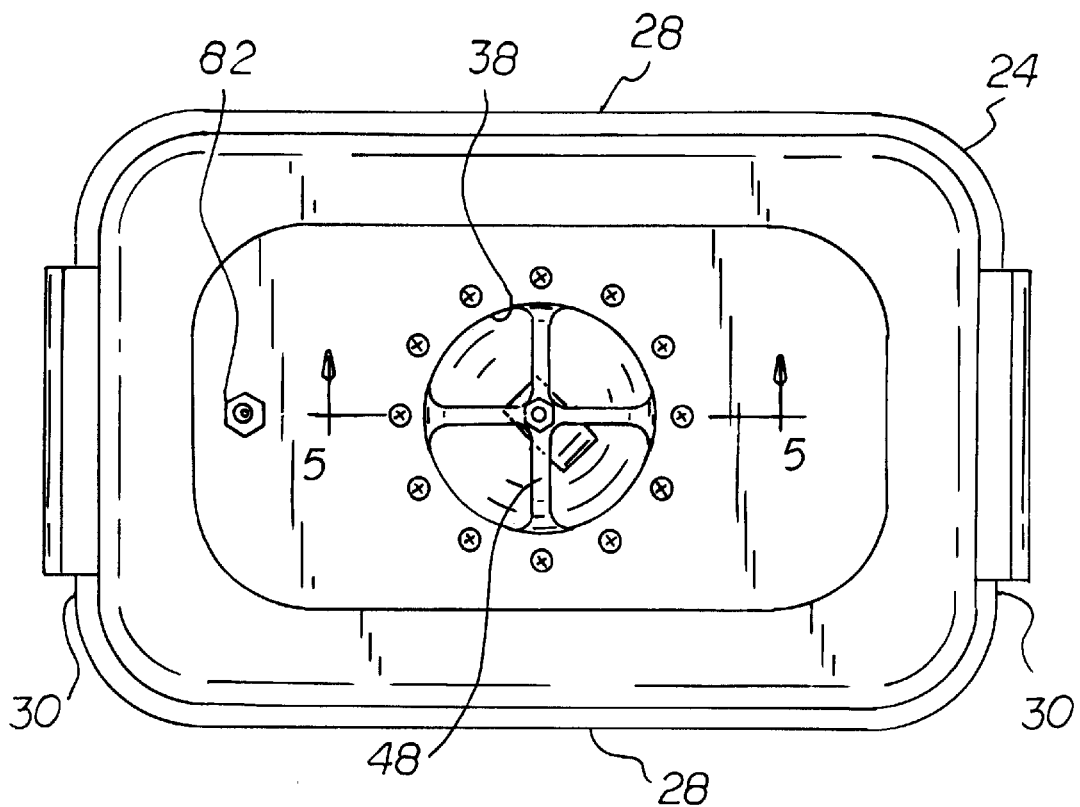
FIG. 2 is a top plan view of the lid taken along line 2—2 of FIG. 1.
Figure 3:
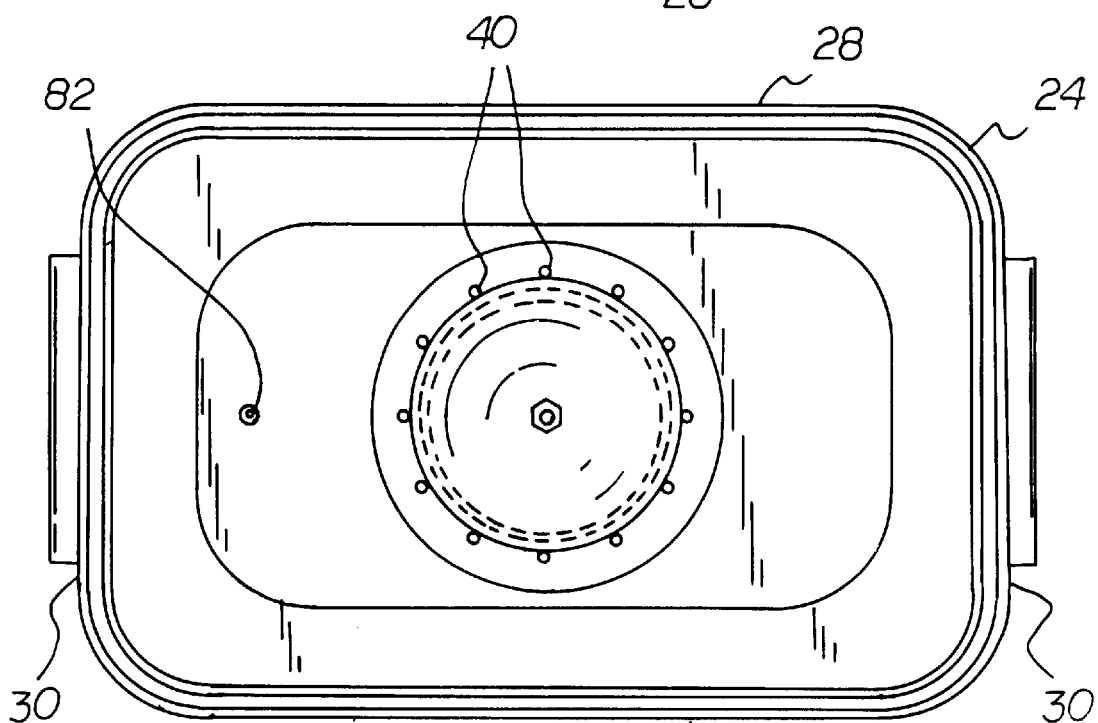
FIG. 3 is a bottom view of the lid taken along line 3—3 of FIG. 1.
Figure 4:
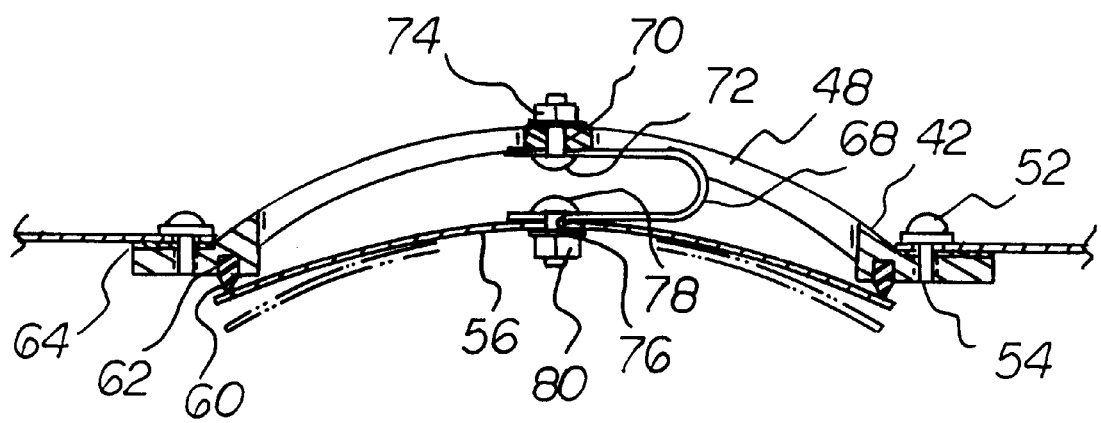
FIG. 4 is a cross-sectional view taken along line 4—4 of FIG. 2.

With reference now to the drawings, and in particular to FIG. 1 thereof, the preferred embodiment of the new and improved flash sterilization container system embodying the principles and concepts of the present invention and generally designated by the reference numeral 10 will be described.

The present invention, the flash sterilization container system 10 is comprised of a plurality of components. Such components in their broadest context include a lid, a support, a thin plate and a ring. Such components are individually configured and correlated with respect to each other so as to attain the desired objective.

First provided is a bottom tray 12. The bottom tray is formed in a generally rectilinear configuration. The bottom tray has a rectangular horizontal bottom wall 14 and rectangular vertical up-standing walls 16, 18. The walls terminate in an upper periphery with an open top 20. In this manner a reception area is formed within the tray for receiving medical instruments to be sterilized. The up-standing walls of the bottom tray include long side walls 16 and short end walls 18. The end walls include releasable clamps 22.

A lid 24 is provided. The lid is formed in a generally rectilinear configuration. The lid has a rectangular horizontal upper wall 26 and rectangular vertical depending walls 28, 30. The walls terminate in a lower periphery with an open bottom 32 positionable on the upper periphery of the tray. The depending walls of the lid include long side walls 28 and short end walls 30. The end walls include reception areas for the releasable clamps to allow locking of the lid to the tray during operation and use. The lid has a large circular aperture 38 through the upper wall. Small attachment apertures 40 are provided through the upper wall adjacent to the large circular aperture.

Provided next is a domed support 42. The domed support is formed with an interior central circular disk 44 and an exterior circular ring 46. Four ribs 48 are provided in a crossing configuration connecting the ring and the disk. The disk has a central aperture 48 there through. A plurality of small attachment apertures 50 are provided through the ring. The apertures are aligned with the small attachment apertures of the lid. Bolts 52 are provided through the attachment apertures of the lid and ring. Associated nuts 54 couple the upper surface of the ring to the lower surface of the upper wall of the lid. The domed support is fabricated of thick stainless steel to preclude expansion upon the application of sterilization heat. The ribs are bowed upwardly to extend through the large aperture of the lid and above the upper surface of the lid.

Also provided is a thin dome shaped plate 56. The plate has an upper surface in contact with the lower surface of the support. The plate is fabricated of a specialty metal. The specialty metal is selected from the class of specialty metals including a nickel alloy and INVAR. INVAR is a trademark of STE. AME. De Commentry Fourchambault Et Decazeville Corporation and relates to an alloy which is substantially inexpasible. Other combinations of metals may be used, i.e., stainless steel and copper. Stainless steel and Invar need not be plated to protect against corrosion, however, other combinations may perform better if protected from corrosion. The plate has a central aperture 58. The periphery of the plate is positionable adjacent to the lower surface of the ring. The plate is adapted to expand upon the application of sterilization heat. In this manner the periphery will move away from the lower surface of the ring.

Provided next is an elastomeric seal 60. The seal is coupled to the lower surface of the ring. The seal has an annular recess 62. The annular recess is formed in the lower surface of the ring for receiving the seal. The seal has a downwardly extending point for contacting the periphery of the plate.

An annular elastomeric gasket 64 is provided next. The gasket is positioned between the ring and the lid. Small attachment apertures 66 are provided in the gasket. The apertures of the gasket are aligned with the attachment apertures of the lid and the ring.

Further provided is a U-shaped spring 68. The spring is also fabricated of a bi-metal. It may be the same material as the disk. The spring is positioned between the disk and the plate. The spring has an upper aperture 70. The upper aperture is aligned with the aperture of the disk. A bolt 72 is provided there through. An associated nut 74 is also provided. The spring has a lower aperture 76. The lower aperture is aligned. with the aperture of the plate. A bolt 78 is provided there through. An associated nut 80 is further provided. The spring couples the plate to the support. The spring and plate are adapted to expand when heated to between about 135 and 272 degrees Fahrenheit, preferably above about 135 degrees Fahrenheit up to a sterilization temperature of about 275 degrees Fahrenheit. In this manner a space is created between the plate and the disk allowing steam to enter the chamber whereby medical instruments within the container may be sterilized. The spring and plate are adapted to close when cooled to above about 135 degrees Fahrenheit. In this manner any space between the plate and the disk will be eliminated.

Next provided is a pressure equalizing valve 82 in the lid. The valve is provided to relieve pressure from the container while heating and cooling.

A protective guard 84 is next provided. The guard is fabricated of stainless steel and formed in two layers. Each layer is perforated with holes 85 preferably of ⅛ inch diameter with centers staggered ³⁄₁₆ inch apart. The holes in the layers are not aligned. The guard is provided to preclude inadvertent manual opening of the valve.

Should the sterilized container be stored, a temperature monitor decal with a temperature sensitive spot will be applied. Indicia reading: "This container's contents not sterile if dot is (a specified color). Reprocess before using." This decal functions as a safety device.

In an alternate embodiment of the present invention the support 86 and plate 88 are flat. In this embodiment, a single bolt 92 passes through the support and plate. An associated nut 94 is provided for coupling purposes.

Figure 6:
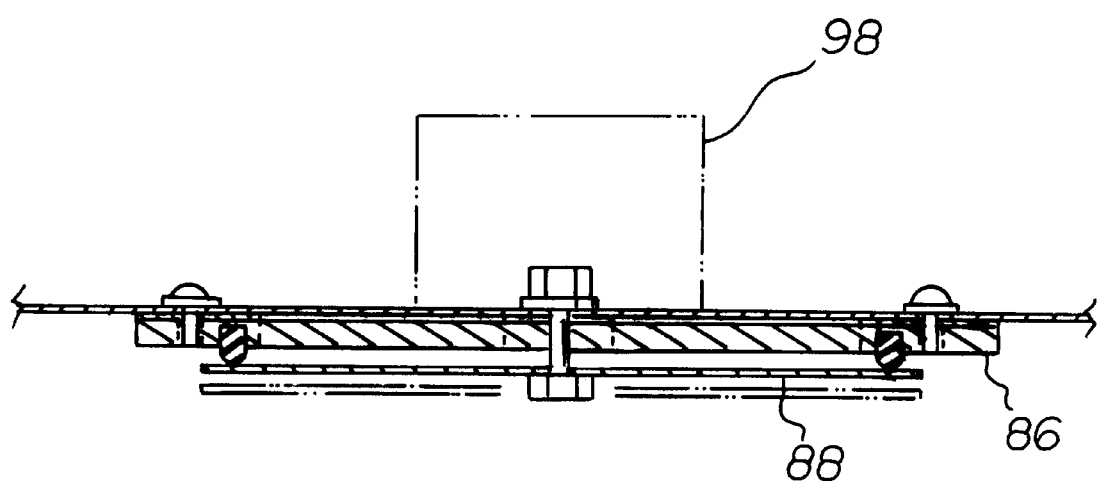
FIG. 6 is a cross-sectional view similar to FIG. 4 but showing an alternate embodiment of the invention.
Figure 5:
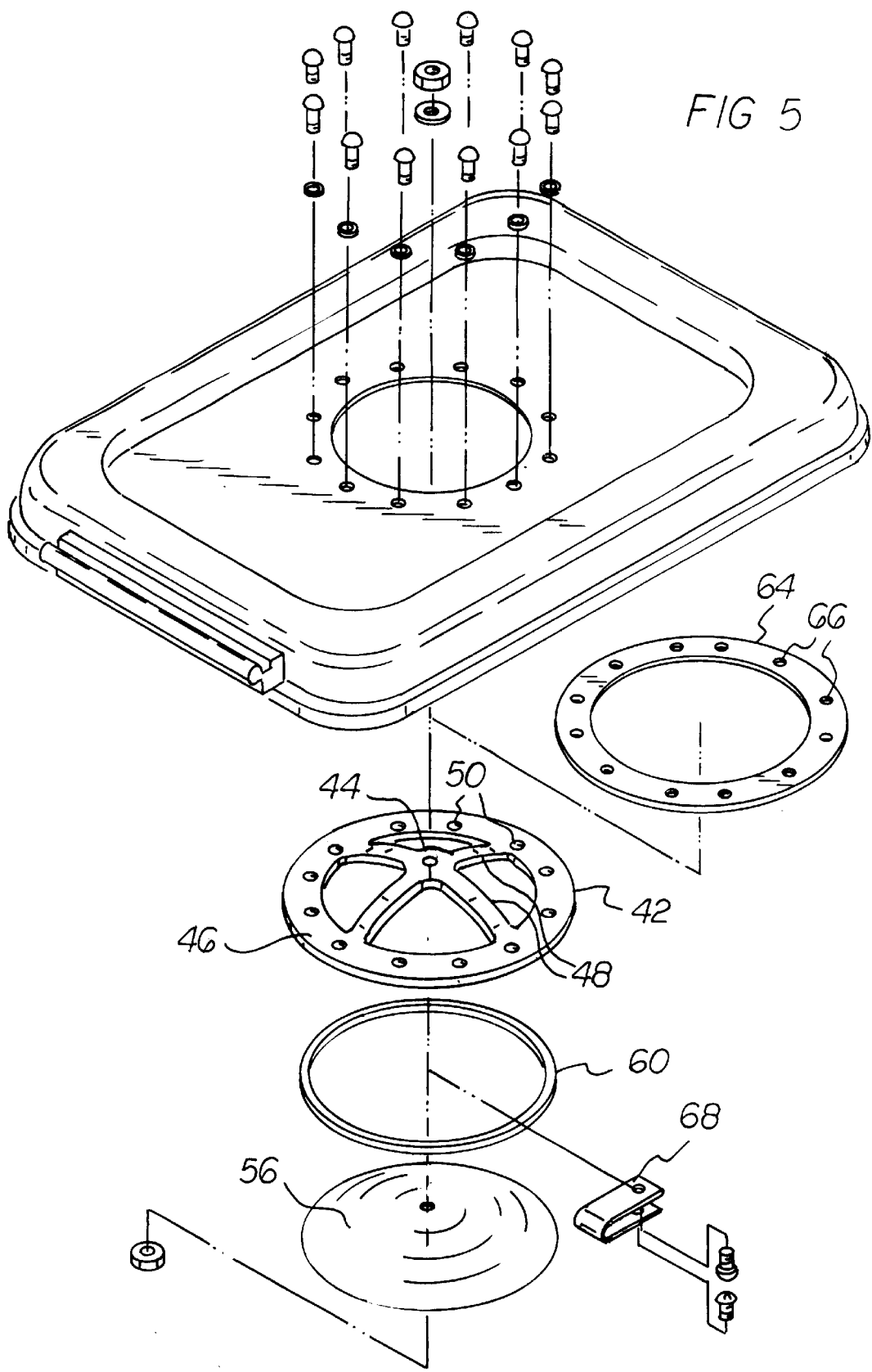
FIG. 5 is an exploded perspective view of system shown in the prior Figure.
Figure 7:
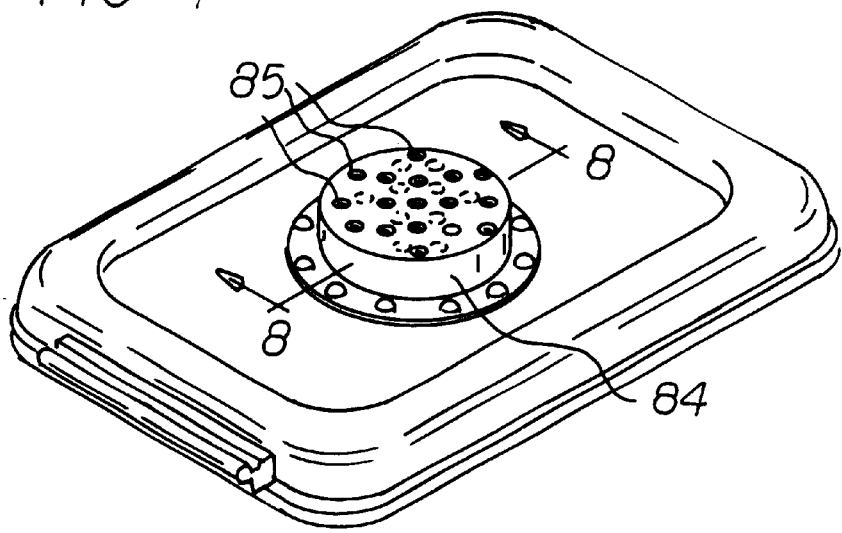
FIG. 7 is a perspective illustration of the invention with the guard in place.
Figure 8:
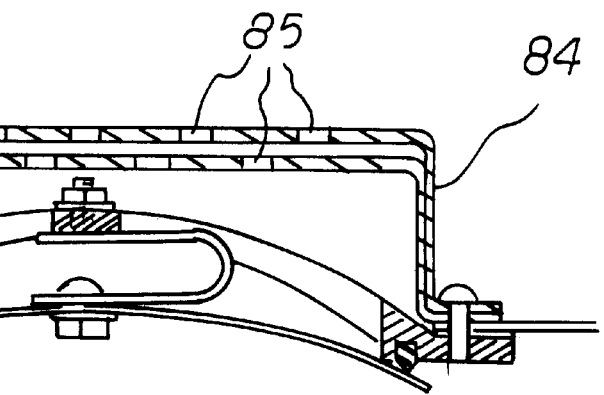
FIG. 8 is a cross-sectional view taken along line 8—8 of FIG. 7.

In still another alternate embodiment of the present invention, as shown in FIG. 6, a timing mechanism 98 is provided as the means to close the disk at a pre-determined time. This embodiment is for use in applications where sterilization is by chemical means rather than by heat.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A sterilization container system for sterilizing medical instruments in an autoclave comprising, in combination:

a bottom tray formed in a generally rectilinear configuration with a rectangular horizontal bottom wall and rectangular vertical up-standing walls terminating in an upper periphery with an open top forming a reception area within the tray for receiving medical instruments to be sterilized, the up-standing walls of the bottom tray including long side walls and short end walls with the end walls including releasable clamps;

a lid formed in a generally rectilinear configuration with a rectangular horizontal upper wall and rectangular vertical depending walls terminating in a lower periphery with an open bottom positionable on the upper periphery of the tray, the depending walls of the lid including long side walls and short end walls with the end walls including reception areas for the releasable clamps to allow locking of the lid to the tray during operation and use, the lid having a large circular aperture through the upper wall with small attachment apertures through the upper wall adjacent to the large circular aperture;

a domed support formed with an interior central circular disk and an exterior circular ring with four ribs in a crossing configuration connecting the ring and the disk, the disk having a central aperture there through and plurality of small attachment apertures through the ring aligned with the small attachment apertures of the lid and with bolts through the attachment apertures of the lid and ring and associated nuts coupling the upper surface of the ring to the lower surface of the upper wall of the lid, the domed support being fabricated of thick 304 stainless steel to preclude expansion upon the application of sterilization heat, the ribs being bowed upwardly to extend through the large aperture of the lid and above the upper surface of the lid;

a thin dome shaped plate having an upper surface in contact with the lower surface of the support and fabricated of a metal elected from a class of substantially inexpansible alloys including nickel alloy the plate having a central aperture and a periphery positionable adjacent to the lower surface of the ring, the plate adapted to expand upon the application of sterilization heat whereby the periphery will move away from the lower surface of the ring;

an elastomeric seal coupled to the lower surface of the ring with an annular recess formed in the lower surface of the ring for receiving the seal, the seal having a downwardly extending point for contacting the periphery of the plate;

an annular elastomeric gasket positioned between the ring and the lid with small attachment apertures there through aligned with the attachment apertures of the lid and the ring;

a U-shaped spring positioned between the disk and the plate with the spring having an upper aperture aligned with the aperture of the disk and a bolt there through with an associated nut and with the spring having a lower aperture aligned with the aperture of the plate and a bolt there through with an associated nut, the spring thus coupling the plate to the support, the spring and plate adapted to expand when heated to above about 135 degrees Fahrenheit up to a sterilization temperature of about 275 degrees Fahrenheit to create a space between the plate and the disk whereby medical instruments within the container may be sterilized, the spring and plate adapted to contract when cooled to above about 135 degrees Fahrenheit to eliminate any space between the plate and the disk;

a pressure equalizing valve in the lid to relieve pressure from the container while cooling while precluding contaminating air from entering the container; and a circular protective guard having a horizontal top and vertical side wall and horizontal attachment areas, the guard fabricated of stainless steel and formed in two layers, each layer perforated with holes of 1/8 inch diameter with centers staggered at about 3/16 inch apart, the holes in one layer being unaligned with the holes in the other layer.

2. A sterilization container system comprising:

a lid with a wall positionable on an upper periphery of a tray, the lid having a large circular aperture and small attachment apertures adjacent to the large circular aperture;

a support formed with an interior central circular disk and an exterior circular ring with ribs connecting the ring and the disk, the disk having a central aperture there through and the ring having plurality of small attachment apertures there through for coupling the upper surface of the ring to the lower surface of the wall;

a thin plate having a central aperture and a periphery positionable adjacent to the lower surface of the ring; and a spring positioned between the disk and the plate, the spring and plate adapted to expand when heated to create a space between the plate and the disk whereby medical instruments within the container system may be sterilized, the spring and plate adapted to contract when cooled to eliminate any space between the plate and the disk.

3. The system as set forth in claim 2 wherein the support and plate are dome shaped and the spring is U-shaped coupling the support and the plate.

4. The system as set forth in claim 2 wherein the support and plate are flat and a single bolt passes through the support and plate and an associated nut for coupling purposes.

5. The system as set forth in claim 2 and further including an elastomeric seal coupled to the lower surface of the ring with an annular recess formed in the lower surface of the ring for receiving the seal.

6. The system as set forth in claim 2 and further including an annular elastomeric gasket positioned between the ring and the lid with small attachment apertures there through aligned with the attachment apertures of the lid and the ring.

7. The system as set forth in claim 2 wherein the spring and plate are adapted to expand upon reaching a temperature of between about 135 and 272 degrees Fahrenheit.

8. A sterilization container system comprising:

a lid with a wall positionable on an upper periphery of a tray, the lid having a large circular aperture and small attachment apertures adjacent to the large circular aperture;

a heat reactive U-shaped spring which will close the container at less than 135 degrees Fahrenheit;

a support formed with an interior central circular disk and an exterior circular ring with ribs connecting the ring and the disk, the disk having a central aperture there through and the ring having a plurality of small attachment apertures there through for coupling the upper surface of the ring to the lower surface of the wall;

a thin plate having a central aperture and a periphery positionable adjacent to the lower surface of the ring.

* * * * *